(12) United States Patent
Kirson et al.

(10) Patent No.: US 11,872,391 B2
(45) Date of Patent: Jan. 16, 2024

(54) ENHANCED-FLEXIBILITY TRANSDUCER ARRAYS FOR DELIVERING TTFIELDS (TUMOR TREATING FIELDS)

(71) Applicant: Novocure GmbH, Root (CH)

(72) Inventors: Eilon Kirson, Haifa (IL); Yoram Wasserman, Haifa (IL); Noa Halavee, Haifa (IL)

(73) Assignee: Novocure GmbH, Root (CH)

( * ) Notice: Subject to any disclaimer, the term of this patent is extended or adjusted under 35 U.S.C. 154(b) by 127 days.

(21) Appl. No.: 17/545,248

(22) Filed: Dec. 8, 2021

(65) Prior Publication Data

US 2022/0096821 A1 Mar. 31, 2022

Related U.S. Application Data

(62) Division of application No. 16/698,269, filed on Nov. 27, 2019, now Pat. No. 11,224,741.

(60) Provisional application No. 62/772,867, filed on Nov. 29, 2018.

(51) Int. Cl.
*A61N 1/04* (2006.01)
*A61N 1/36* (2006.01)

(52) U.S. Cl.
CPC ......... *A61N 1/0492* (2013.01); *A61N 1/0496* (2013.01); *A61N 1/36002* (2017.08); *A61N 1/0476* (2013.01)

(58) Field of Classification Search
CPC .. A61N 1/0476; A61N 1/0492; A61N 1/0496; A61N 1/36002
See application file for complete search history.

(56) References Cited

U.S. PATENT DOCUMENTS

| 6,868,289 | B2 | 3/2005 | Palti |
| 7,016,725 | B2 | 3/2006 | Palti |
| 7,089,054 | B2 | 8/2006 | Palti |
| 7,136,699 | B2 | 11/2006 | Palti |
| 7,146,210 | B2 | 12/2006 | Palti |
| 7,333,852 | B2 | 2/2008 | Palti |
| 7,467,011 | B2 | 12/2008 | Palti |
| 7,519,420 | B2 | 4/2009 | Paiti |
| 7,565,205 | B2 | 7/2009 | Palti |
| 7,565,206 | B2 | 7/2009 | Paiti |

(Continued)

FOREIGN PATENT DOCUMENTS

| JP | 2016508825 A | 3/2016 |
| WO | 2015036420 A1 | 3/2015 |
| WO | 2016014264 A1 | 1/2016 |

OTHER PUBLICATIONS

International Search Report and Written Opinion issued in application No. PCT/IB2019/060259 dated Feb. 28, 2020.

*Primary Examiner* — Amanda K Hulbert
(74) *Attorney, Agent, or Firm* — Potomac Law Group, PLLC

(57) ABSTRACT

A transducer array for use in tumor-treating fields (TT-Fields) therapy is particularly suited for use in treating abdominal or thoracic cancers. The transducer array has features that increase its flexibility and adhesion to the patient's skin, including a branching configuration and a correspondingly branching top covering adhesive-backed layer. Additionally, a skin-level adhesive layer is provided beneath the flex circuit to which the electrode elements are attached, to help ensure thorough, lasting adhesion of the transducer array to the patient's skin over the course of treatment.

16 Claims, 12 Drawing Sheets

(56) References Cited

U.S. PATENT DOCUMENTS

| | | |
|---|---|---|
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,440,068 B2 | 9/2016 | Palti et al. |
| 9,655,669 B2 | 5/2017 | Palti et al. |
| 9,731,106 B2 | 8/2017 | Peterson |
| 9,750,934 B2 | 9/2017 | Palti et al. |
| 9,910,453 B2 | 3/2018 | Wasserman et al. |
| 10,188,851 B2 | 1/2019 | Wenger et al. |
| 10,441,776 B2 | 10/2019 | Kirson et al. |
| 10,779,875 B2 | 9/2020 | Palti et al. |
| 10,821,283 B2 | 11/2020 | Giladi et al. |
| 10,967,167 B2 | 4/2021 | Hagemann et al. |
| 11,013,909 B2 | 5/2021 | Wenger et al. |
| 11,103,698 B2 | 8/2021 | Chang et al. |
| 2006/0167499 A1 | 7/2006 | Palti |
| 2007/0239213 A1 | 10/2007 | Palti |
| 2010/0204560 A1 | 8/2010 | Salahieh et al. |
| 2012/0283726 A1 | 11/2012 | Palti |
| 2016/0331961 A1 | 11/2016 | Bianchi |
| 2016/0346530 A1 | 12/2016 | Jeffery et al. |
| 2017/0120041 A1 | 5/2017 | Wenger et al. |
| 2017/0215939 A1 | 8/2017 | Palti et al. |
| 2017/0281934 A1 | 10/2017 | Giladi et al. |
| 2017/0354816 A1 | 12/2017 | Huelman et al. |
| 2018/0001075 A1 | 1/2018 | Kirson et al. |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2019/0117956 A1 | 4/2019 | Wenger et al. |
| 2019/0307781 A1 | 10/2019 | Krex et al. |
| 2019/0308016 A1 | 10/2019 | Wenger et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0016399 A1 | 1/2020 | Kaynan et al. |
| 2020/0023179 A1 | 1/2020 | Bomzon et al. |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0121728 A1 | 4/2020 | Wardak et al. |
| 2020/0129761 A1 | 4/2020 | Bomzon et al. |
| 2020/0155835 A1 | 5/2020 | Wasserman et al. |
| 2020/0171297 A1 | 6/2020 | Kirson et al. |
| 2020/0179512 A1 | 6/2020 | Giladi et al. |
| 2020/0219261 A1 | 7/2020 | Shamir et al. |
| 2020/0269041 A1 | 8/2020 | Zeevi et al. |
| 2020/0269043 A1 | 8/2020 | Wasserman et al. |
| 2020/0306531 A1 | 10/2020 | Tran et al. |
| 2020/0330755 A1 | 10/2020 | Wasserman et al. |
| 2020/0368525 A1 | 11/2020 | Maag et al. |
| 2021/0008367 A1 | 1/2021 | Giladi et al. |
| 2021/0031031 A1 | 2/2021 | Wasserman et al. |
| 2021/0038584 A1 | 2/2021 | Voloshin-Sela |
| 2021/0060334 A1 | 3/2021 | Avraham et al. |
| 2021/0069503 A1 | 3/2021 | Tran et al. |
| 2021/0196348 A1 | 7/2021 | Wasserman |
| 2021/0199640 A1 | 7/2021 | Patel et al. |
| 2021/0203250 A1 | 7/2021 | Wasserman |
| 2021/0268247 A1 | 9/2021 | Story et al. |
| 2021/0299440 A1 | 9/2021 | Deslauriers et al. |
| 2021/0308446 A1 | 10/2021 | Alon et al. |
| 2021/0330950 A1 | 10/2021 | Hagemann et al. |
| 2021/0346694 A1 | 11/2021 | Wasserman et al. |

ENHANCED-FLEXIBILITY TRANSDUCER ARRAYS FOR DELIVERING TTFIELDS (TUMOR TREATING FIELDS)

CROSS REFERENCE TO RELATED APPLICATIONS

This application is a divisional of U.S. application Ser. No. 16/698,269, filed Nov. 27, 2019, which claims the benefit of U.S. Provisional Application 62/772,867, filed Nov. 29, 2018, each of which are incorporated herein by reference in their entirety.

FIELD OF THE INVENTION

This application is directed to transducer arrays (i.e., arrays of electrode elements) used to treat cancer with tumor-treating electric fields ("TTFields therapy"). More particularly, it is directed to transducer arrays with enhanced flexibility to facilitate their use in treating, for example, thoracic or abdominal cancers.

BACKGROUND

In general, TTFields therapy is a cancer therapy that uses electric fields tuned to specific frequencies to disrupt cell division, thereby inhibiting tumor growth and causing affected cancer cells to die. With TTFields therapy, transducers arrays are placed on opposite sides of the body, with intimate contact between the electrodes and the patient's skin, and an AC voltage is applied between opposing arrays at a predetermined frequency to generate the required electric fields. TTFields therapy typically continues for many months or even years, during which time the transducer arrays are replaced every 5-10 days.

In practice, the transducer arrays are provided and applied to the body as a unitary or self-contained unit, with the electrode elements arrayed throughout the self-contained unit. The array of electrode elements is affixed to the body, typically using an overlying patch with an adhesive backing to cover the unit and hold it against the patient's skin.

Known configurations of such transducer arrays have been developed in connection with treating Glioblastoma, in which case the transducer arrays are attached to the head. Because the skull is substantially rigid and immobile, good adhesion and lasting attachment of the transducer arrays to the skin can be obtained until such time that the transducer arrays require replacement.

On the other hand, the thoracic and abdominal regions of the body are far more mobile than the skull is, due to general movement of the body and respiration. This substantially increased degree of movement can cause the transducer arrays not to adhere to thoracic and abdominal regions with the degree of intimacy of contact and/or duration of contact that may be desired. Higher levels of perspiration from these areas also make it more challenging to achieve good long-term, intimate adhesion of the transducer arrays to the skin.

SUMMARY OF THE INVENTION

One aspect of the invention is directed to a first electrode apparatus configured for affixation to a patient's skin. The first apparatus comprises a flex circuit having a trunk region that extends in a longitudinal direction and a plurality of branches that extend laterally from the trunk region, each of the branches having a free distal end and a proximal end that is connected to the trunk region, with a plurality of branches extending on at least one lateral side of the trunk region, the flex circuit having an inner skin-facing side and an outer side. The first apparatus also comprises a plurality of electrode elements disposed on the inner side of the flex circuit along the branches of the flex circuit, each of the electrode elements having a conductive plate that is connected to the flex circuit in an electrically conducting manner, and a dielectric layer positioned to face the skin of the patient. The first apparatus also comprises a top, covering layer disposed on the outer side of the flex circuit, the covering layer being sized to cover the branches of the flex circuit and to overlap spaces between the branches, the covering layer having adhesive on a skin-facing side thereof by means of which the covering layer can be adhered to the patient's skin through the spaces between the branches. The covering layer is slotted to define a plurality of fingers overlying the branches of the flex circuit so that the fingers of the covering layer can move independently of each other as branches of the flex circuit flex independently of each other.

Some embodiments of the first apparatus further comprise a plurality of conductive hydrogel discs, wherein each of the conductive hydrogel discs is attached to a skin-facing side of a respective electrode element. Some of these embodiments further comprise a plurality of gel barriers, wherein each of the gel barriers surrounds a respective one of the hydrogel discs.

Some embodiments of the first apparatus further comprise a foam layer disposed on the inner side of the flex circuit, wherein the foam layer is configured to cover at least a portion of the trunk region of the flex circuit and at least a portion of the branches of the flex circuit, and leave the electrode elements uncovered. Some of these embodiments further comprise a skin-level adhesive layer disposed on a skin-facing side of the foam layer. In some of these embodiments, the skin-level adhesive layer has a configuration that follows the configuration of the flex circuit, with branches and trunk portions of the skin-level adhesive layer being wider than corresponding portions of the flex circuit so as to overlap spaces between the branches of the flex circuit.

In some embodiments of the first apparatus, more electrode elements are attached to branches of the flex circuit that are closer to the longitudinal center of the trunk than are attached to branches of the flex circuit that are farther from the longitudinal ends of the trunk. In some embodiments of the first apparatus, the trunk shifts back and forth in the lateral direction as it extends in the longitudinal direction. In some embodiments of the first apparatus, the trunk extends in the longitudinal direction in a straight manner.

Some embodiments of the first apparatus further comprise a skin-level adhesive layer disposed on the inner side of the flex circuit. In some of these embodiments, the skin-level adhesive layer has a configuration that follows the flex circuit, with branches and trunk portions of the skin-level adhesive layer being wider than corresponding portions of the flex circuit so as to overlap spaces between the branches of the flex circuit.

Some embodiments of the first apparatus further comprise a skin-level adhesive layer disposed on the inner side of the flex circuit, wherein the skin-level adhesive layer is attached directly to the inner side of the flex circuit.

In some embodiments of the first apparatus, the flex circuit has a plurality of branches extending on each lateral side of the trunk region. In some embodiments of the first apparatus, the flex circuit is configured so that no more than three paths emanate from any intersection on the flex circuit. In some embodiments of the first apparatus, the flex circuit is configured so that four paths emanate from only a single intersection on the flex circuit, and no more than three paths emanate from any other intersection on the flex circuit. In some embodiments of the first apparatus, the flex circuit is configured so that all segments of the flex circuit are straight.

Some embodiments of the first apparatus further comprise an electrical cable that terminates on the flex circuit, and segments of the flex circuit near the distal end of each branch are thinner than at least some of the segments of the flex circuit that are adjacent to the electrical cable.

Another aspect of the invention is directed to a second electrode apparatus configured for affixation to a patient's skin. The second apparatus comprises a flex circuit having a trunk region that extends in a longitudinal direction and a plurality of branches that extend laterally from the trunk region, each of the branches having a free distal end and a proximal end that is connected to the trunk region, with a plurality of branches extending on at least one lateral side of the trunk region, the flex circuit having an inner skin-facing side and an outer side. The second apparatus also comprises a plurality of electrode elements disposed on the inner side of the flex circuit along the branches of the flex circuit, each of the electrode elements having a conductive plate that is connected to the flex circuit in an electrically conducting manner, and a dielectric layer positioned to face the skin of the patient. The second apparatus also comprises a foam layer disposed on the inner side of the flex circuit, wherein the foam layer is configured to cover at least a portion of the trunk region of the flex circuit and at least a portion of the branches of the flex circuit, and leave the electrode elements uncovered. The second apparatus also comprises a skin-level adhesive layer disposed on a skin-facing side of the foam layer. The second apparatus also comprises a top, covering layer disposed on the outer side of the flex circuit, the covering layer being sized to cover the branches of the flex circuit and to overlap spaces between the branches, the covering layer having adhesive on a skin-facing side thereof by means of which the covering layer can be adhered to the patient's skin through the spaces between the branches.

Some embodiments of the second apparatus further comprise a plurality of conductive hydrogel discs, wherein each of the conductive hydrogel discs is attached to a skin-facing side of a respective electrode element. Some of these embodiments further comprise a plurality of gel barriers, wherein each of the gel barriers surrounds a respective one of the hydrogel discs.

In some embodiments of the second apparatus, more electrode elements are attached to branches of the flex circuit that are closer to the longitudinal center of the trunk than are attached to branches of the flex circuit that are farther from the longitudinal ends of the trunk.

In some embodiments of the second apparatus, the trunk shifts back and forth in the lateral direction as it extends in the longitudinal direction.

In some embodiments of the second apparatus, the trunk extends in the longitudinal direction in a straight manner.

In some embodiments of the second apparatus, the covering layer is slotted to define a plurality of fingers overlying the branches of the flex circuit so that the fingers of the covering layer can move independently of each other as branches of the flex circuit flex independently of each other. In some embodiments of the second apparatus, the flex circuit has a plurality of branches extending on each lateral side of the trunk region. In some embodiments of the second apparatus, the foam layer is configured to cover the entire surface of the flex circuit, except for regions where the electrode elements are positioned.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Figure 1:
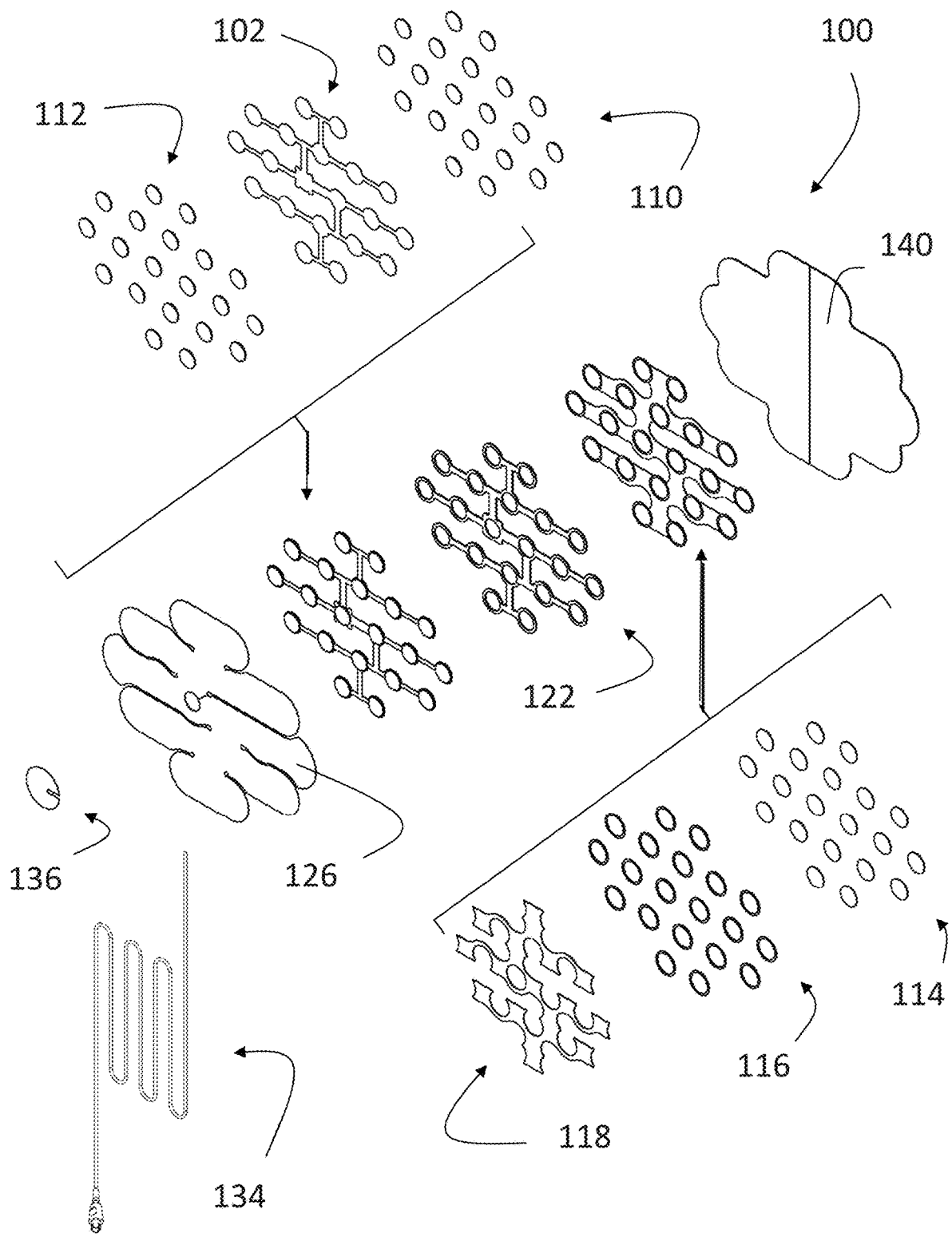
FIG. 1 is an exploded view of one embodiment of a transducer array that has a first layout of electrode elements.

FIGS. 1-12 depict a first embodiment of a transducer array 100 (also referred to herein as an "electrode apparatus") with a first layout of electrode elements, with FIG. 1 being an exploded or assembly view showing all of the various components and their arrangement relative to each other. FIGS. 2-12 show the individual components in greater detail.

One of the components that defines the configuration of the transducer array 100 is the flex circuit 102 (FIGS. 1 and 2), which may be made with electrical traces extending along the branches of the flex circuit as is well known in the art. The flex circuit 102 has a branching or ramified configuration. There is a central trunk 108a-108g that extends in a longitudinal direction. There are also a plurality of branches that extend laterally from both sides of the trunk of the flex circuit 102. In some embodiments (including the embodiments depicted in FIGS. 1, 2, and 8), these branches are perpendicular to the longitudinal direction and are arranged as rows 106a-106e of the flex circuit. In the illustrated embodiment, each of the rows of the flex circuit includes two branches—one on either side of the trunk segments 108a-108g. The proximal end of each branch is connected to and extends from the trunk of the flex circuit 102, while the distal end of each branch remains free. Advantageously, this configuration improves the flexibility of the flex circuit 102, and it reduces tensile stresses applied on the transducer array 100 by skin movement (bending, stretching, twisting, breathing, etc.), thereby improving and prolonging adhesion of the array 100 to the skin. It also improves user comfort and reduces skin damage. Note that in the embodiment illustrated in FIGS. 1 and 2, the trunk 108a-108g shifts back and forth in segments between successive rows of the flex circuit. In these embodiments, only some of the segments 108a, 108c, 108e, and 108g extend in the longitudinal direction, and those longitudinal segments are interconnected by additional segments 108b, 108d, and 108f that extend in the lateral direction. As a result, in these embodiments, the trunk shifts back and forth in the lateral direction as it extends in the longitudinal direction. In alternative embodiments (see, e.g., trunk 108 in the FIG. 13 and FIG. 14 embodiments) the trunk is straight.

The flex circuit 102 includes a number of mounting pads 104 arranged along the rows 106a-106e.

A number of electrode elements 110 (FIGS. 1 and 3)—for example, twenty as shown in the FIGS. 1-12 embodiment for a typically sized adult male—are disposed on the inner (i.e., skin-facing) side of the mounting pads 104 of the flex circuit 102 (shown in FIGS. 1 and 2) with an electrically conductive connection between each of the electrode elements 110 and the flex circuit 102. The electrode elements 110 may be on the order of 1 mm thick and 2 cm in diameter and may optionally be slightly smaller in diameter than the mounting pads 104. Each of the electrode elements 110 may be formed from a circular conductive plate that is coated with a ceramic dielectric material as is known in the art, and the circular conductor is electrically connected to an electrical contact of the flex circuit 102. The ceramic dielectric material faces toward the patient's body so it can make contact with the patient's skin (preferably via an intervening layer of hydrogel, as described below).

A corresponding number of stiffeners 112 (FIGS. 1 and 4) may optionally be attached to the outer side of the mounting pads 104 of the flex circuit 102. The stiffeners 112 may be on the order of 1 mm thick and may be slightly smaller in diameter than the mounting pads 104. The stiffeners 112 may be made from any suitable material (e.g., a stiff, nonconductive plastic). In general, the stiffeners 112 help prevent the electrode elements 110 from breaking, given the flexible nature of the flex circuit 102 and the thin, fragile nature of the ceramic dielectric used for the electrode elements 110.

In some embodiments, each of the electrode elements 110 has a corresponding disc of conductive hydrogel 114 (FIGS. 1 and 5) disposed on the inner side of the electrode element, to establish good electrical conductivity with the patient's skin. In some embodiments, the disc of hydrogel 114 is slightly larger in diameter than the electrode. The material is preferably gamma sterilization-compatible. For example, the hydrogel discs 114 may be made from AG625, which is available from Axelgaard, with a thickness on the order of 635 micrometers, and with a volume resistivity of 1000 ohm-cm max.

Additionally, a ring-shaped hydrogel barrier 116 (FIGS. 1, 6A, and 6B) is optionally provided, surrounding each of the hydrogel discs 114. In general, the hydrogel barriers 116 help maintain the integrity of the hydrogel 114 throughout the duration of wear and prevent migration of the hydrogel from its correct location under the electrode elements 110. The hydrogel barriers 116 may be made, e.g., from MED 5695R, available from Vancive Medical Technologies, which is a polyethylene foam, and may be single-coated with WetStick™ synthetic rubber adhesive, also available from Vancive Medical Technologies. The hydrogel barriers 116 may be 500 micrometers thick, and are preferably gamma sterilization-compatible.

To increase patient comfort, the transducer array 100 may optionally include a conformal foam layer 122 (FIGS. 1, 8A, and 8B) positioned beneath the flex circuit 102, and shaped to closely follow the branching configuration of the flex circuit 102. Note that unlike the flex circuit 102 (which has solid circular mounting pads 104 for the electrode elements 110), the foam layer 122 has ring-shaped regions 124 that surround the electrode elements so as not to intervene between the electrode elements 110 and the patient's skin. A suitable thickness for the conformal foam layer 122 is on the order of 1 mm, and the foam layer 122 is preferably the same thickness as the electrode elements 110. The foam layer 122 preferably covers the entire surface of the flexible flex circuit 102 (except for the regions where the electrode elements 110 are positioned) while maintaining overall flexibility and conformability of the transducer array 100. But in alternative embodiments, the foam layer 122 only covers a portion of the surface of the flexible flex circuit 102. In some embodiments, the size of the foam layer 122 may be minimized to the extent possible so as not to reduce the overall breathability and fluid-vaporizing properties of the transducer array 100.

The conformal foam layer 122 may be made, e.g., from polyethylene foam such as MED 5696R available from Vancive Medical Technologies. The conformal foam layer 122 may be affixed to the flex circuit 102 using a suitable adhesive (e.g., WetStick™ synthetic rubber adhesive, also available from Vancive Medical Technologies). The foam layer 122 advantageously protects the patient from potentially sharp edges of the conductive traces on the flex circuit 102. This is particularly important in the context of flexible transducer arrays because flexing the transducer arrays can cause the flat conductive traces to twist, which can cause the potentially sharp edges of those conductive traces to tilt down towards the patient's skin. Notably, interposing the foam layer 122 between the conductive traces of the flex circuit 102 and the patient's skin protects the patient from cuts and/or pain that might be caused by those potentially sharp edges.

Figure 7A:
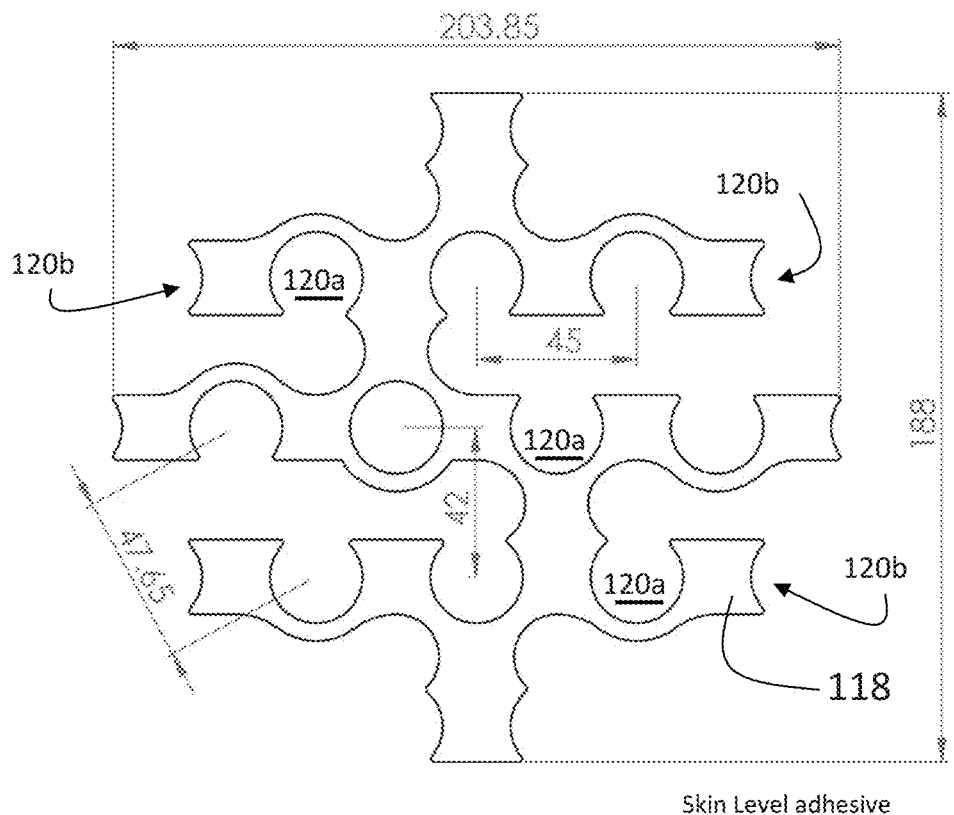
FIG. 7A is a plan view of a skin-level adhesive layer used in the transducer array illustrated in FIG. 1.
Figure 7B:
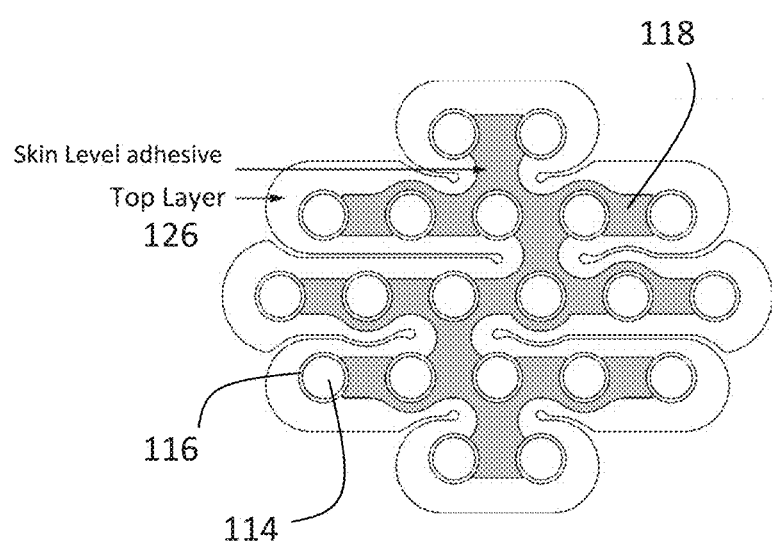
FIG. 7B is a view of the hydrogel discs, hydrogel barriers, and skin-level adhesive layer as "seen" by the patient's skin.
Figure 8A:
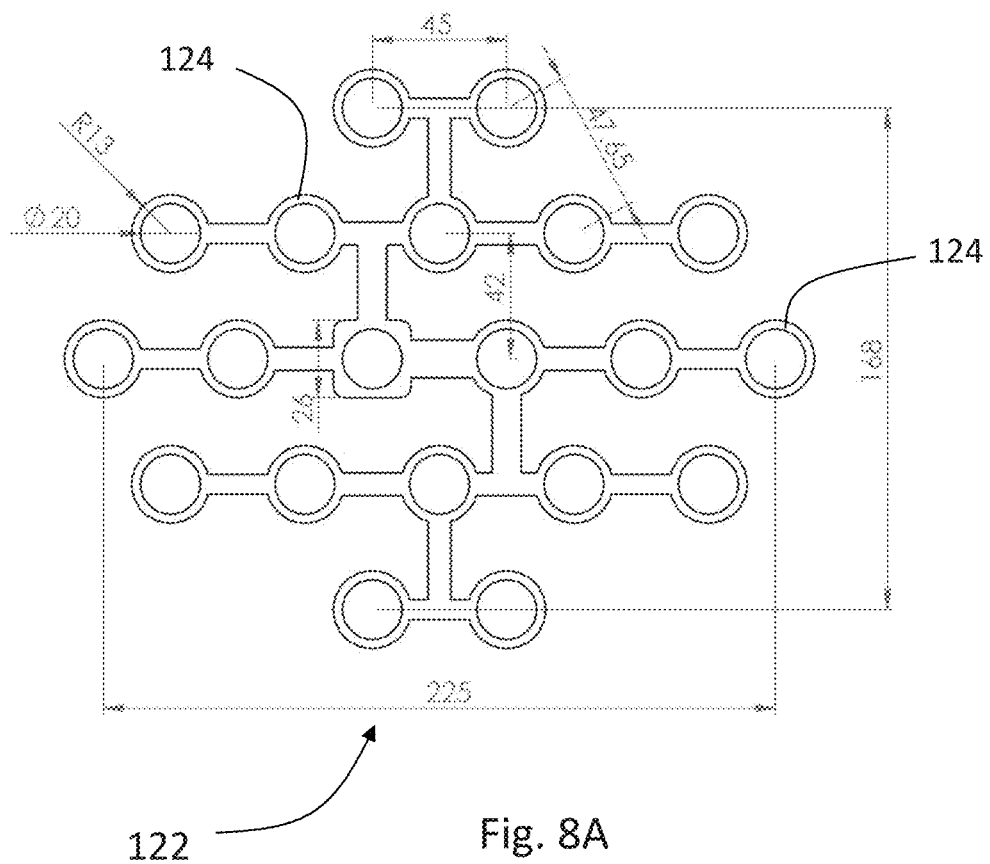
FIG. 8A is a plan view of a foam layer used in the transducer array illustrated in FIG. 1.
Figure 8B:
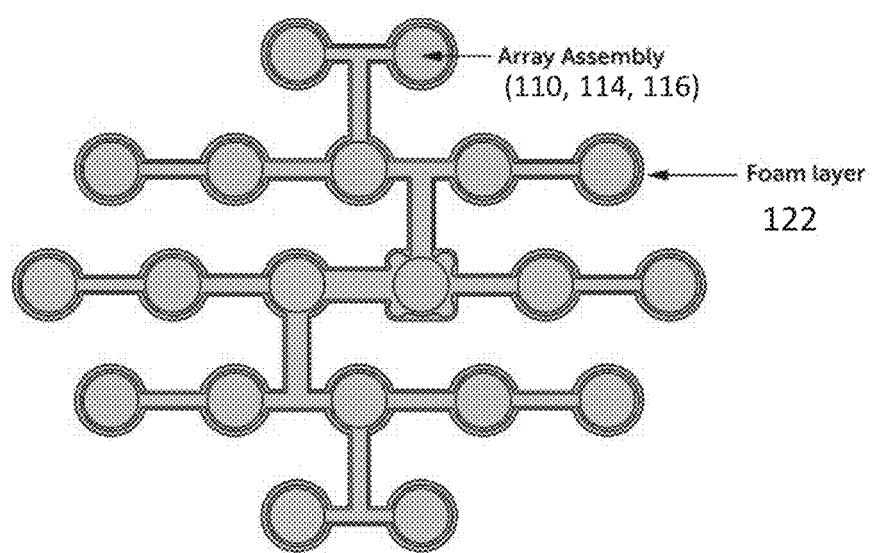
FIG. 8B is a view of the electrode elements and the foam layer as "seen" by the patient's skin.
Figure 9:
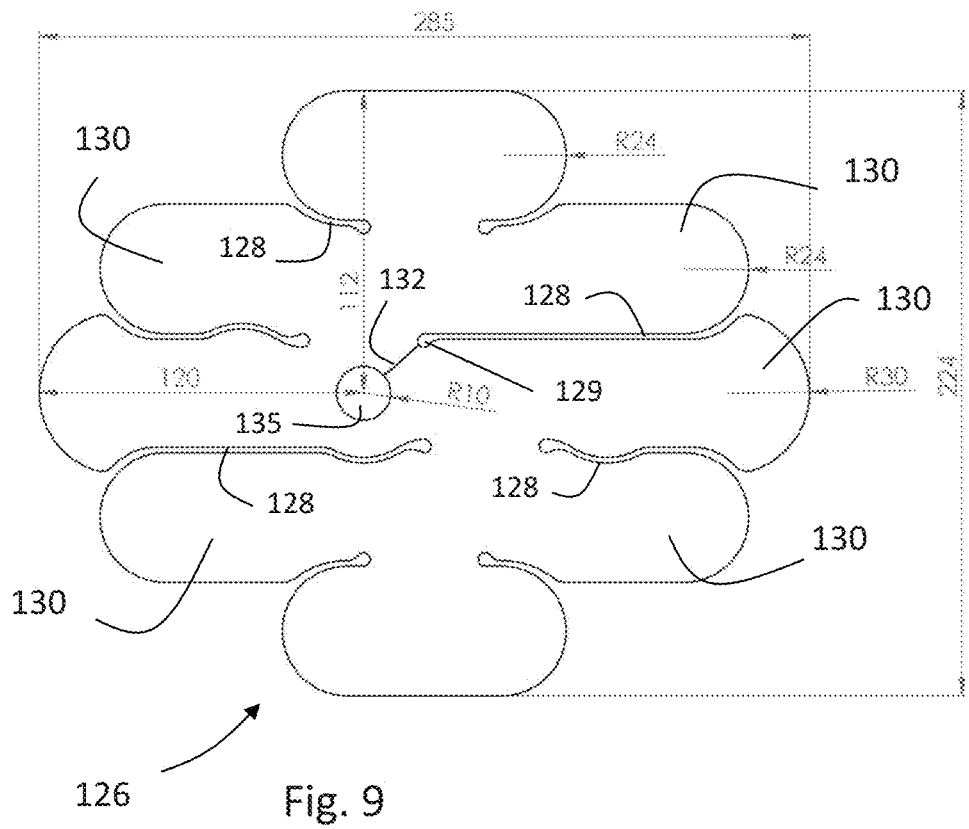
FIG. 9 is a plan view of a top, covering adhesive-backed layer used in the transducer array illustrated in FIG. 1.

The transducer array 100 also includes a skin-level layer of adhesive 118 disposed beneath the foam layer 122, as shown in FIGS. 1, 7A, and 7B. (The skin-level adhesive 118 also appears in FIG. 6B.) In general, the skin-level layer of adhesive 118 follows the branching configuration of the flex circuit 102 and the foam layer 122, but with the various branches and trunk portions of the skin-level adhesive 118 being slightly wider than the corresponding portions of the flex circuit 102 and the foam layer 122 so as to at least partially overlap with the spaces between the branches of the flex circuit 102 and the foam layer 122. Notably, the skin-level adhesive 118 includes cutouts 120a along the branches of the adhesive, and cutouts 120b at the free ends of the branches of the adhesive. These cutouts 120a, 120b are shaped so as not to intervene between the electrode elements 110 and the patient's skin. The skin-level layer of adhesive also functions as a constructive element, to stabilize the central area around the electrode elements.

The skin-level layer of adhesive 118 may be made from a polyester/rayon-blend, spunlace non-woven tape material such as 3M® 9917, which is 30 micrometers thick. The tape may be double-coated with acrylate adhesive, to provide a peel strength on the skin-facing side (e.g., 23 lbf/inch) and a higher peel strength (e.g., 27 lbf/inch) on the opposite, outer side. The material is preferably hypoallergenic, highly conformable, and breathable; with a high moisture vapor transmission rate; and it is preferably gamma sterilization-compatible. To prevent excessive sweating and moisture from being trapped under the transducer array 100, the overall surface area of the skin-level layer of adhesive 118 may be minimized, e.g., by making it just slightly wider than the corresponding portions of the flex circuit 102 and the foam layer 122.

Note that in embodiments where a conformal foam layer 122 is omitted, the layer of adhesive 118 would be connected directly to the flex circuit 102 with no intervening components disposed therebetween. Alternatively, in those embodiments where the conformal foam layer 122 is provided, the layer of adhesive 118 would be connected indirectly to the flex circuit 102, with a foam layer 122 disposed therebetween.

A top, covering adhesive-backed layer 126 (FIGS. 1, 9, and 11) is positioned above the outer side of the flex circuit 102. The covering adhesive-backed layer 126 has a number of slots 128, which divide the covering adhesive-backed layer 126 into a number of separate fingers 130, each of which overlies a respective branch of the flex circuit 102. The slots 128 are preferably significantly narrower than the fingers 130 and the fingers 130 are preferably wider than the diameters of the electrode elements. This configuration results in the fingers 130 of the covering adhesive-backed layer 126 overlapping with the spaces between the branches of the flex circuit 102 to provide maximal adhesion of the covering adhesive-backed layer 126 to the patient's skin around the electrode elements, while still allowing the fingers 130 of the covering adhesive layer to move independently of each other as the branches of the flex circuit 102 move independently of each other. This, in turn, helps to maintain conformability of the transducer array 100 and adhesion to the patient's skin even as the patient moves. In addition, the covering adhesive-backed layer 126 preferably extends beyond the perimeter of the flex circuit 102 to provide additional adhesion to the skin at the outer boundary of the transducer array 100.

The covering adhesive-backed layer 126 may be made from 3M® 9916, which is a 100% polyester, spunlace non-woven tape. This material is single-coated with acrylate adhesive on the skin-facing side, which adheres the covering adhesive-backed layer 126 to the outer surface of the flex circuit 102, and it has a thickness of 40 micrometers. The covering adhesive-backed layer 126 is preferably hypoallergenic, highly conformable, breathable, and gamma sterilization-compatible.

Notably and advantageously, two separate factors contribute to the adhesion of the entire transducer array 100 to the patient's skin. The first factor is the portions of the lower surface of the top adhesive layer 126 that contact the skin through the spaces between the branches of the flex circuit 102 and beyond the perimeter of the flex circuit 102. The second factor is the layer of adhesive 118 disposed between the foam layer 122 and the person's skin (or, between the flex circuit 102 and the person's skin in those embodiments that do not include the foam layer 122). The inclusion of these two separate adhesive components provides significantly improve adhesion of the transducer array 100 to the patient's skin. This feature of the transducer array 100 enhances the degree of adhesion of the transducer array 100 to the patient's skin around the electrode elements, resulting in prolonged and better skin/electrode contact as compared to configurations in which the only adhesion was provided by an adhesive-backed patch overlying the entire transducer array.

In some embodiments, the covering adhesive-backed layer 126 includes a central aperture 135 and a slit 132 extending from the innermost end 129 of one of the slots 128—in particular, the innermost slit-end that is closest to the central aperture 135. The central aperture 135 permits an electrical cable 134 (shown in FIG. 11) that protrudes from the back surface of the flex circuit to extend through the covering adhesive-backed layer 126. This electrical cable 134 is used to connect the flex circuit 102 to a TTFields therapy controller (not illustrated) via a connector. The slit 132 is useful for positioning the adhesive-backed layer 126 over the flex circuit 102 after the cable 134 has been connected to the flex circuit 102 during the assembly process. In particular, portions of the covering adhesive-backed layer 126 can be moved away from each other to open the slit 132, such that the covering adhesive-backed layer 126 can be passed around the electrical cable 134 on either side and then the entire adhesive-backed layer can be pressed into proper position.

Figure 10:
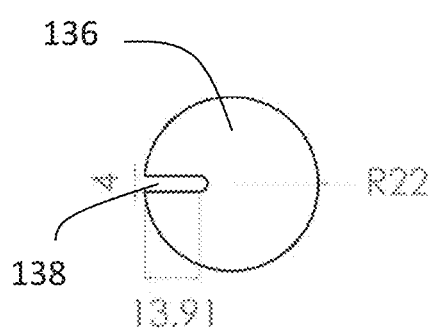
FIG. 10 is a plan view of a slot cover used in the transducer array illustrated in FIG. 1.
Figure 11:
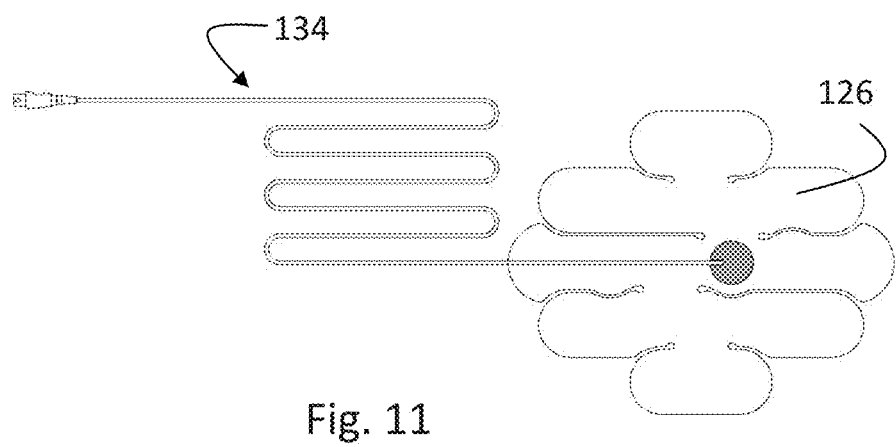
FIG. 11 is a plan view illustrating the appearance of a transducer array as illustrated in FIG. 1 as applied to a patient.

Once the transducer array 100 has been properly attached to the patient's skin with the covering adhesive-backed layer 126 securing it in place, the central aperture 135 may be covered, for protection, with a top adhesive-backed slot-cover 136 (FIGS. 1, 10, and 11). The slot-cover 136 may be a disc-shaped item, formed from the same material and in the same manner as the covering adhesive-backed layer 126. In some preferred embodiments, the slot cover 136 includes a slot 138 for the electric cable 134 to pass through.

Figure 12:
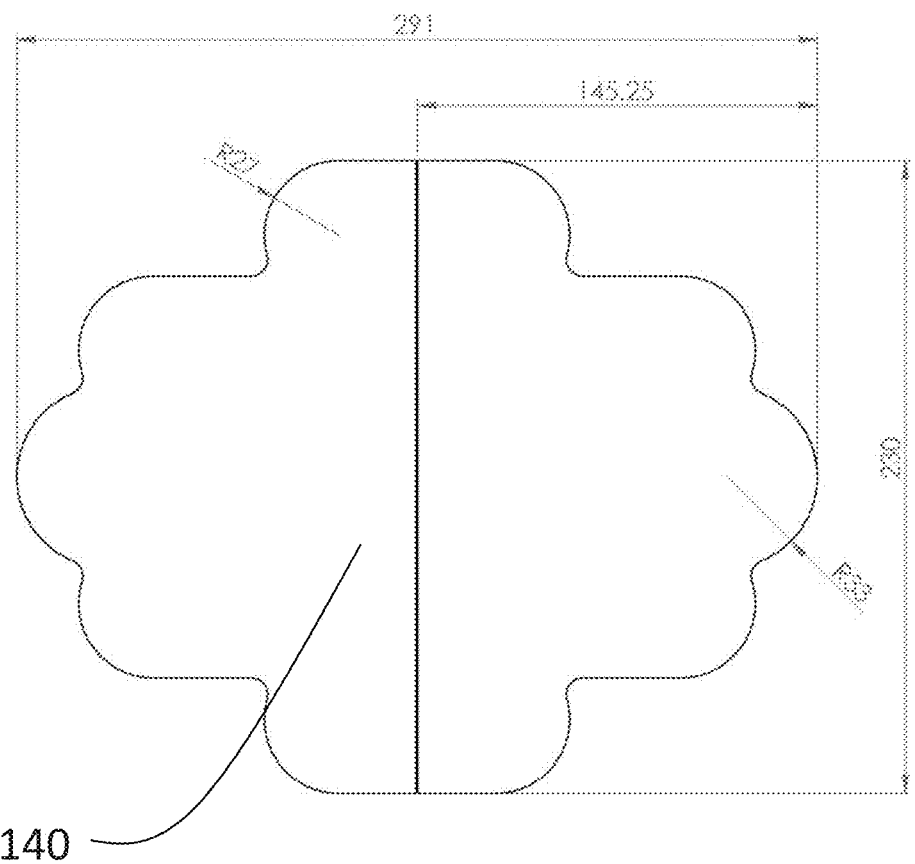
FIG. 12 is a plan view of a release liner used in the transducer array illustrated in FIG. 1.

In some preferred embodiments, the entire assembly of components described above is protected, prior to use on a patient, with a two-part release liner 140 (FIGS. 1 and 12). The release liner has an overall shape that generally follows, but may be slightly larger than, the outer periphery of the covering adhesive-backed layer 126. It may be made e.g., from AR W4000, available from Adhesive Research, which is a white, silicone-coated PET (polyethylene terephthalate) material that is 50 micrometers thick.

Figure 13:
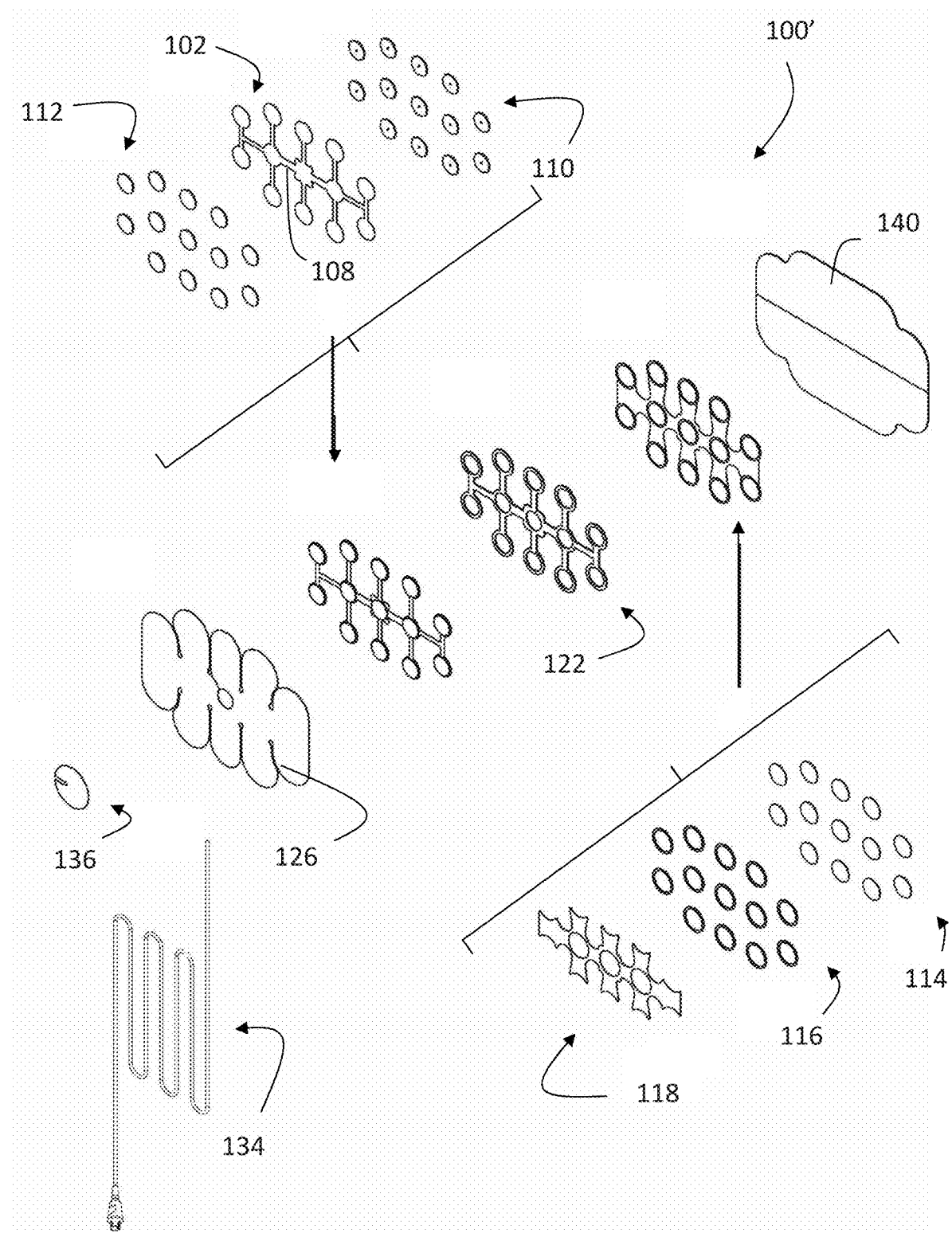
FIG. 13 is an exploded view of another embodiment of a transducer array that has a different layout of electrode elements.

In the FIGS. 1-12 embodiment of a transducer array 100 described above, there are 20 electrode elements arranged in five rows, with two, five, six, five, and two electrode elements in each of the successive rows. (The rows correspond with the branches of the flex circuit and are perpendicular to the longitudinal direction in which the trunk extends. Thus, the rows are oriented horizontally and the trunk is oriented vertically as the transducer array 100 is oriented in FIG. 1 and the flex circuit 102 is oriented in FIG. 2.) Depending on factors such as the size, sex, age, etc. of a patient, however, there could be more or less electrode elements arranged in different configurations, while still adhering to the inventive concepts disclosed herein. For example, as illustrated in FIG. 13, there could be 13 electrode elements arranged in five rows (rows oriented vertically in FIG. 13), with there being two, three, three, three, and two electrode elements in successive rows and with the rows being interconnected by a trunk 108 of the transducer array that extends in a straight line all the way across the device (trunk oriented horizontally in FIG. 13). Furthermore, in both illustrated embodiments, there are more electrode elements in the rows that are closer to the longitudinal center of the trunk than there are in the rows that are closer to the longitudinal ends of the trunk. In other embodiments (not illustrated), there could be the same number of electrode elements in all rows, i.e., along all branches of the flex circuit.

In both the FIGS. 1-12 embodiment and the FIG. 13 embodiment, the flex circuit 102 has a plurality of branches extending on each lateral side of the trunk region. But in alternative embodiments, the branches may be present only on a single lateral side of the trunk region (in which case, the trunk region would be located near one edge of the apparatus.

Figure 14:
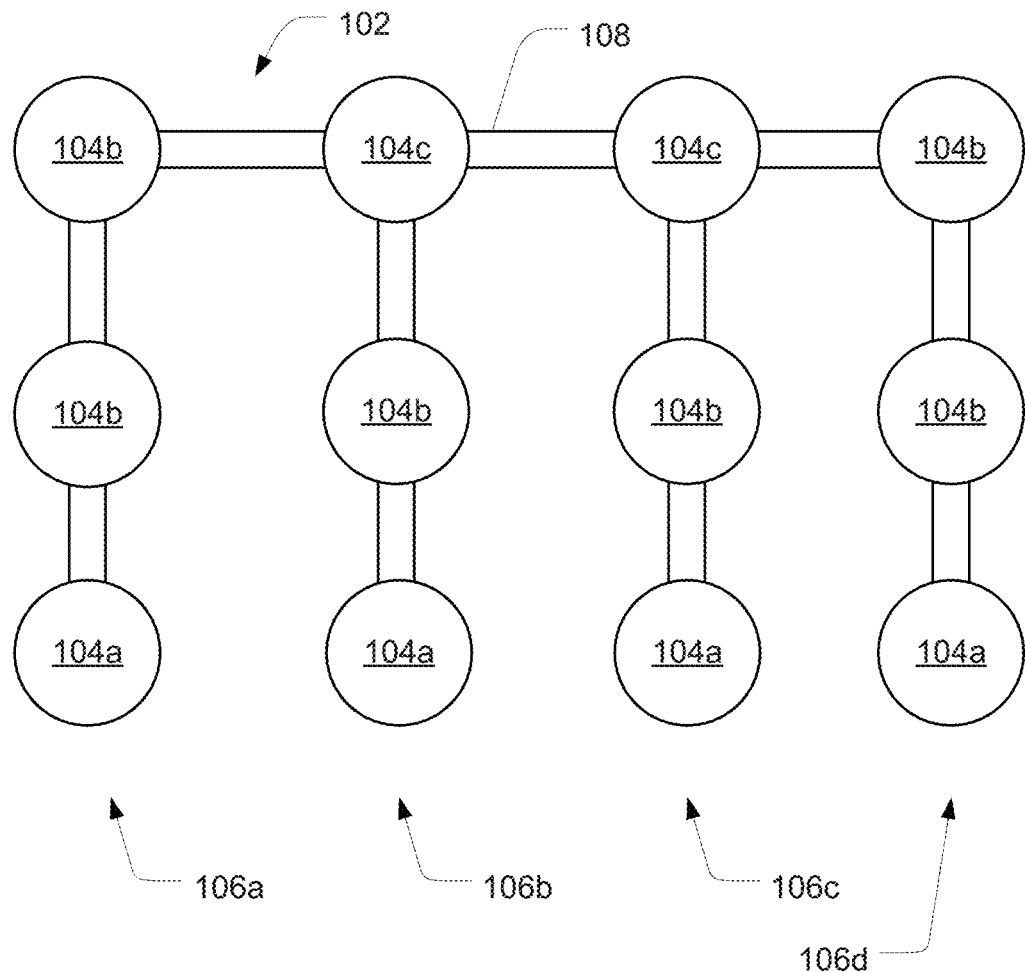
FIG. 14 is a plan view of the flex circuit of another embodiment in which branches are present only on a single lateral side of the trunk region.

FIG. 14 depicts an example of a configuration in which the branches are present only on a single lateral side of the trunk region. In this embodiment, the flex circuit 102 has a linear trunk 108, a plurality of branches 106a-106d, and a plurality of mounting pads 104a-104c positioned on those branches. The remaining elements in this embodiment such as the stiffeners, the electrode elements, the foam layer, the hydrogel, the hydrogel barrier, the skin layer adhesive, the top covering adhesive backed layer, the electrical cable, and the slot cover, etc. (not shown) are similar to the corresponding elements in the FIG. 1-12 embodiment, except that the positioning of those elements follows the structure of the FIG. 14 layout as opposed to the structure of the FIG. 2 layout. As explained above in connection with the FIG. 2 embodiment, positioned above the outer side of the flex circuit 102 is an adhesive-backed layer that has a number of slots. These slots divide the covering adhesive-backed layer into a number of separate fingers, each of which overlies a respective branch of the flex circuit 102. This configuration allows the fingers of the covering adhesive layer to move independently of each other as the branches of the flex circuit 102 move independently of each other. This, in turn, helps to maintain flexibility and conformability of the transducer array and adhesion to the patient's skin even as the patient moves.

Figure 2:
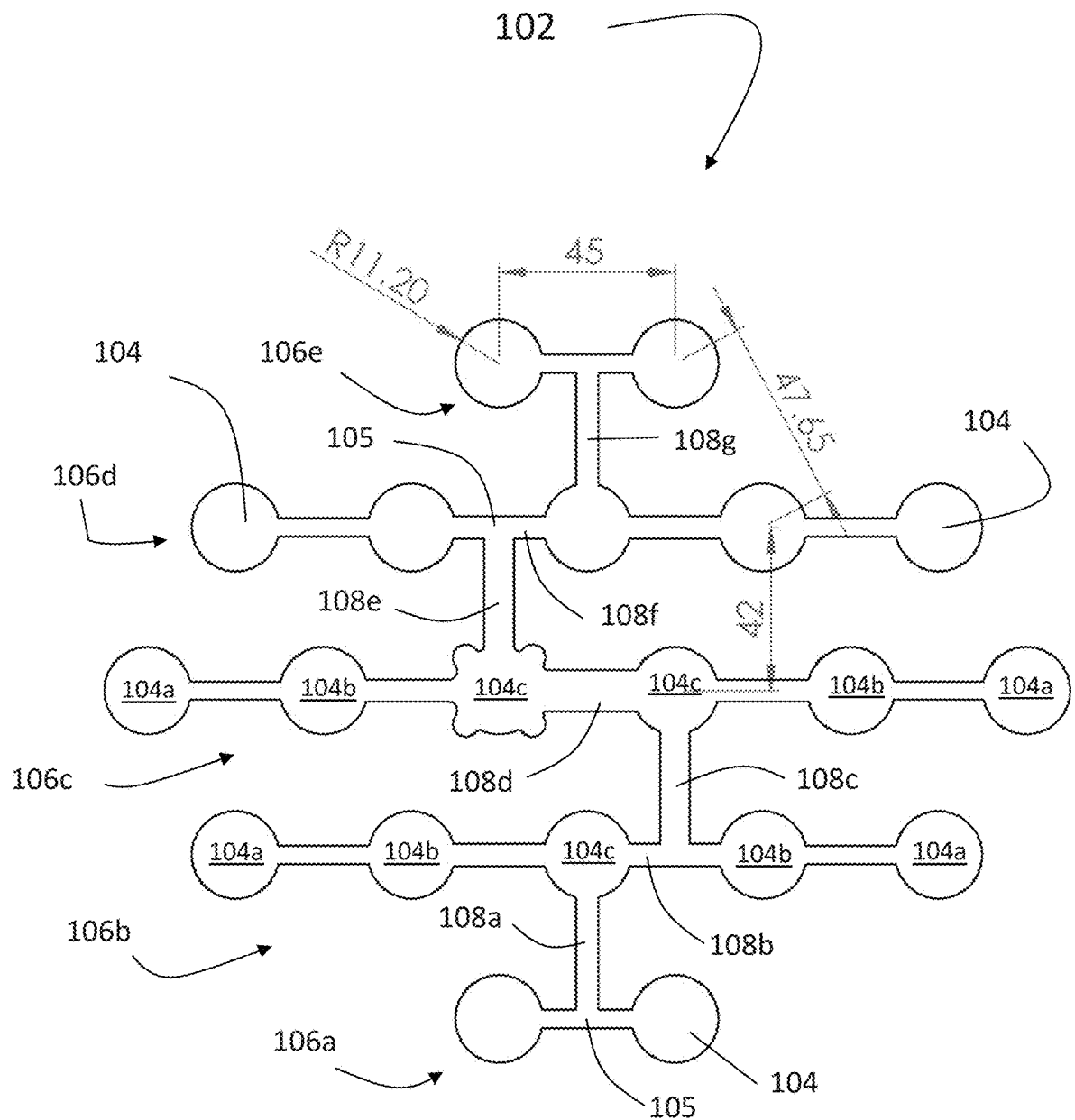
FIG. 2 is a plan view of the flex circuit used in the transducer array illustrated in FIG. 1.
Figure 3:
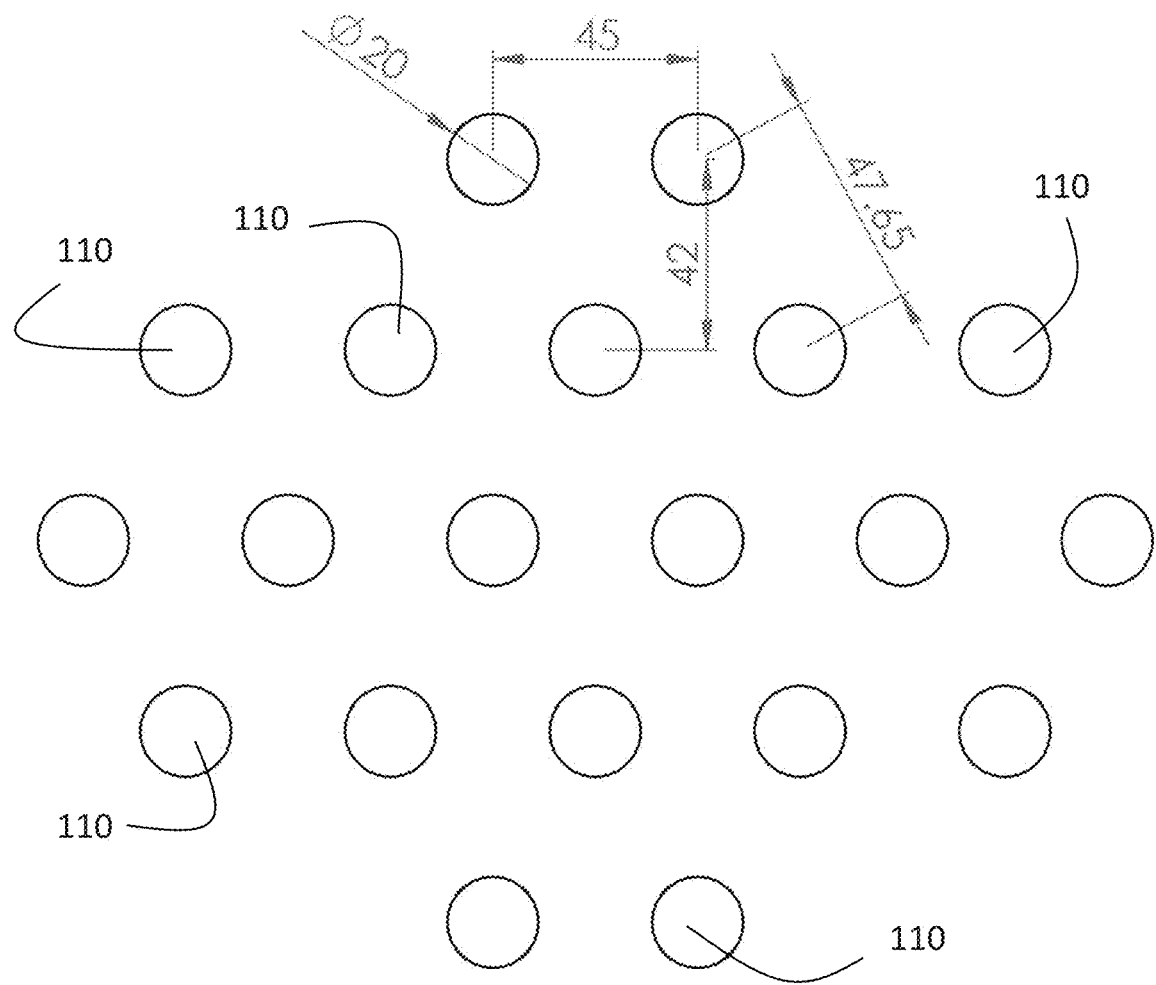
FIG. 3 is a plan view of the electrode elements used in the transducer array illustrated in FIG. 1.
Figure 4:
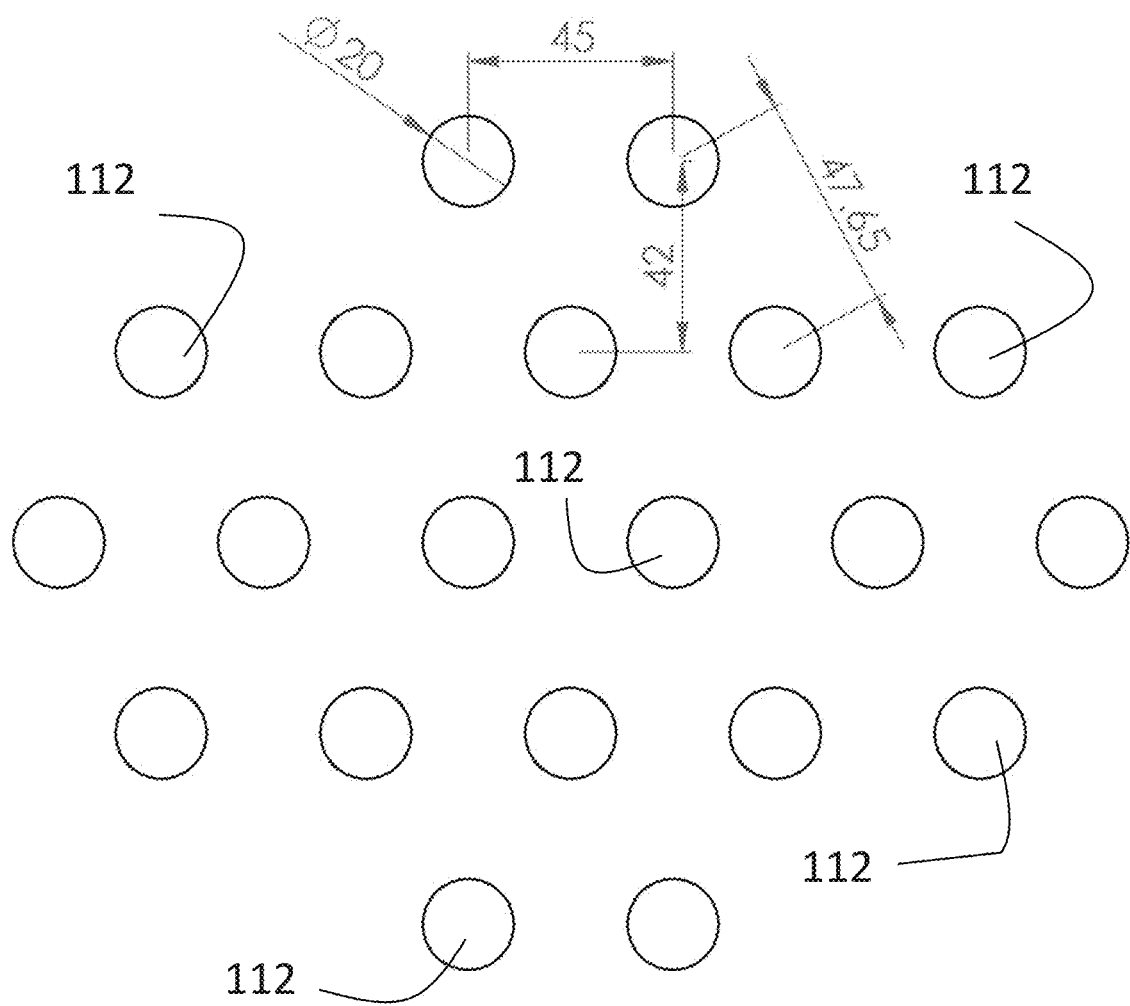
FIG. 4 is a plan view of stiffeners used in the transducer array illustrated in FIG. 1.
Figure 5:
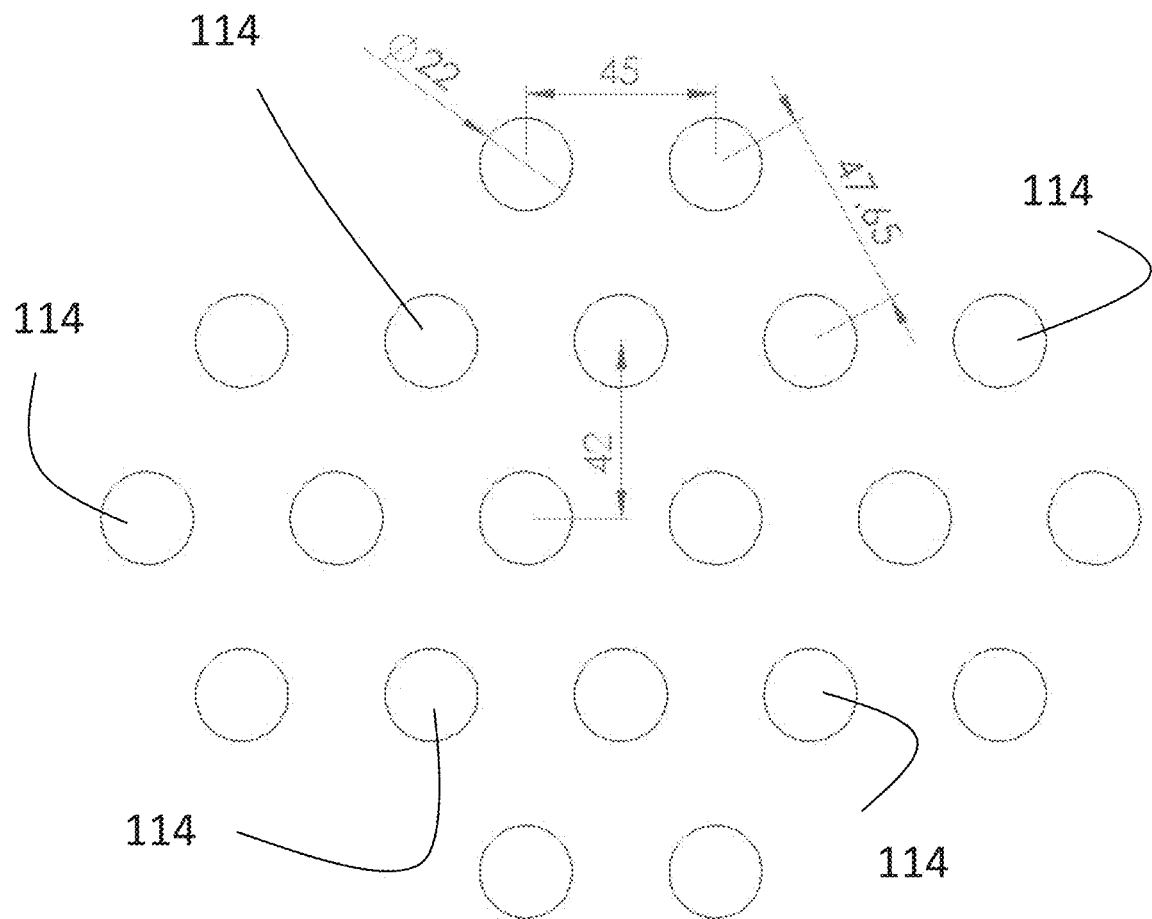
FIG. 5 is a plan view of conductive hydrogel discs used in the transducer array illustrated in FIG. 1.
Figure 6A:
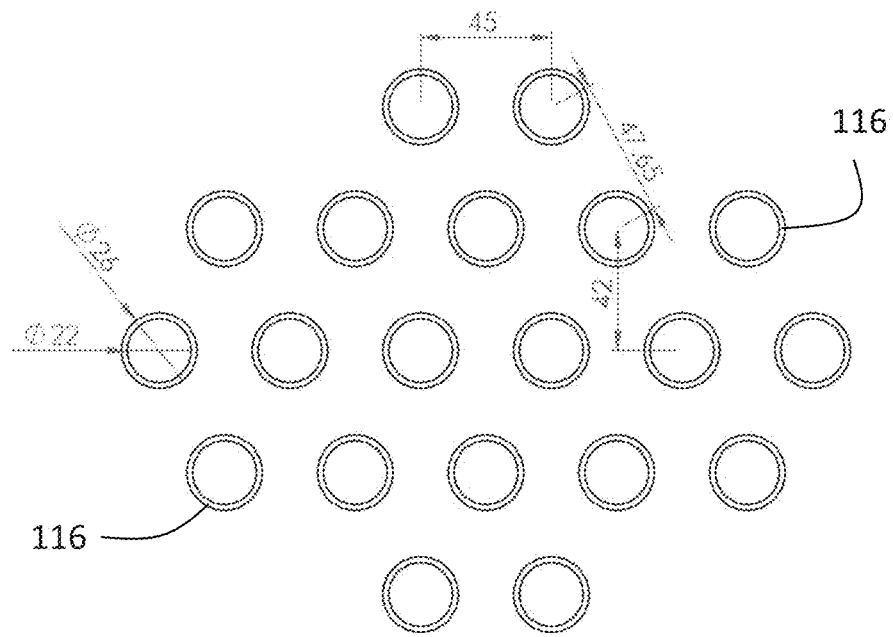
FIG. 6A is a plan view of hydrogel barriers used in the transducer array illustrated in FIG. 1.
Figure 6B:
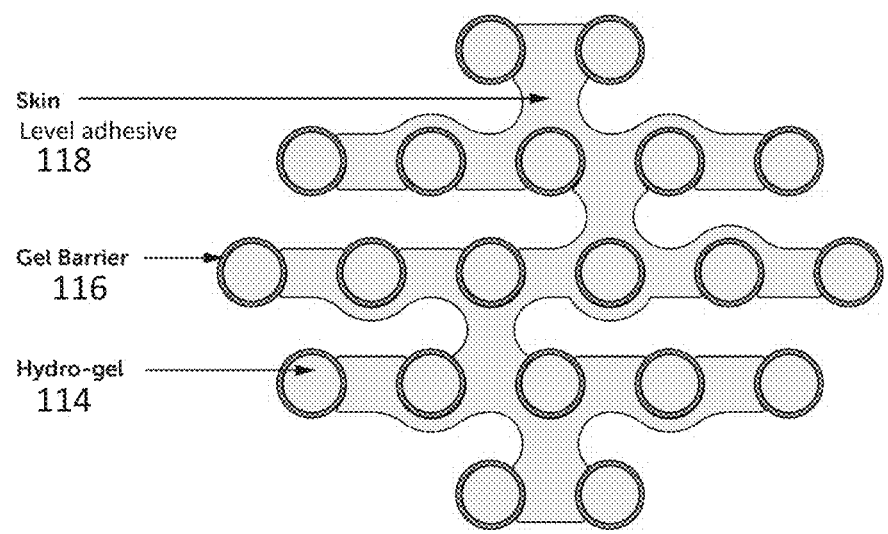
FIG. 6B is a view of the hydrogel discs and hydrogel barriers as "seen" by the patient's skin.

In some embodiments (including but not limited to the FIGS. 1-12 embodiment) the flex circuit is configured so that no more than three paths emanate from any given intersection on the flex circuit. This is best explained in connection with FIG. 2, from which it is apparent that one path of the flex circuit emanates from the intersections at the mounting pads 104a, two paths of the flex circuit emanate from the intersections at the mounting pads 104b, and three paths of the flex circuit emanate from the intersections at the mounting pads 104c. Notably, there are no intersections on the flex circuit 102 from which more than three paths emanate. This holds true for both the intersections that are positioned at the mounting pads 104, and also for intersections that are not positioned at one of the mounting pads 104 (e.g., The T-shaped intersections 105). The FIG. 14 embodiment similarly has no intersections on the flex circuit 102 from which more than three paths emanate. Configuring the flex circuit 102 so that there are no intersections from which more than three paths emanate (e.g., as depicted in FIGS. 2 and 14) improves the flexibility of the flex circuit, which advantageously improves the flexibility of the entire apparatus.

In alternative embodiments (e.g., the FIG. 13 embodiment), intersections do exist from which four paths emanate (see, e.g., the three mounting pads in the center of the apparatus). In other alternative embodiments (not shown) only a single intersection exists from which four paths emanate.

In some preferred embodiments, including the FIGS. 1-12 and FIG. 13 embodiments, all segments of the flex circuit are straight.

In some preferred embodiments, including the FIGS. 1-12 and FIG. 13 embodiments, an electrical cable terminates on the flex circuit (as best seen in FIG. 11). Optionally, in these embodiments, (as best seen in FIG. 2) segments of the flex circuit 102 near the distal end of each branch are thinner than at least some of the segments of the flex circuit 102 that are adjacent to the location where the electrical cable terminates (e.g., segment 108d). This configuration increases the flexibility of the flex circuit, which also contributes to improving the flexibility of the entire apparatus.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An electrode apparatus configured for affixation to a patient's skin, comprising:
   a flex circuit having a trunk region that extends in a longitudinal direction and a plurality of branches that extend laterally from the trunk region, each of the branches having a free distal end and a proximal end that is connected to the trunk region, with a plurality of branches extending on at least one lateral side of the trunk region, the flex circuit having an inner skin-facing side and an outer side;
   a plurality of electrode elements disposed on the inner side of the flex circuit along the branches of the flex circuit, each of the electrode elements having a conductive plate that is connected to the flex circuit in an electrically conducting manner, and a dielectric layer positioned and adapted to be facing the skin of the patient;
   a foam layer disposed on the inner side of the flex circuit, wherein the foam layer is configured to cover at least a portion of the trunk region of the flex circuit and at least a portion of the branches of the flex circuit, and leave the electrode elements uncovered;
   a skin-level adhesive layer disposed on a skin-facing side of the foam layer; and
   a top, covering layer disposed on the outer side of the flex circuit, the covering layer being sized to cover the branches of the flex circuit and to overlap spaces between the branches, the covering layer having adhesive on a skin-facing side thereof by means of which the covering layer can be adhered to an underlying surface through the spaces between the branches.

2. The electrode apparatus of claim 1, further comprising a plurality of conductive hydrogel discs wherein each of the conductive hydrogel discs is attached to a skin-facing side of a respective electrode element.

3. The electrode apparatus of claim 1, wherein the covering layer is slotted to define a plurality of fingers overlying the branches of the flex circuit so that the fingers of the covering layer can move independently of each other as branches of the flex circuit flex independently of each other.

4. The electrode apparatus of claim 1, wherein the flex circuit has a plurality of branches extending on each lateral side of the trunk region.

5. The electrode apparatus of claim 1, wherein the foam layer is configured to cover the entire surface of the flex circuit, except for regions where the electrode elements are positioned.

6. The electrode apparatus of claim 2, further comprising a plurality of gel barriers, wherein each of the gel barriers surrounds a respective one of the hydrogel discs.

7. The electrode apparatus of claim 1, wherein more electrode elements are attached to branches of the flex circuit that are closer to the longitudinal center of the trunk than are attached to branches of the flex circuit that are closer to the longitudinal ends of the trunk.

8. The electrode apparatus of claim 1, wherein the trunk shifts back and forth in the lateral direction as it extends in the longitudinal direction.

9. The electrode apparatus of claim 1, wherein the trunk extends in the longitudinal direction in a straight manner.

10. The electrode apparatus of claim 1, wherein the skin-level adhesive layer has a configuration that follows the configuration of the flex circuit, with branches and trunk portions of the skin-level adhesive layer being wider than corresponding portions of the flex circuit so as to overlap spaces between the branches of the flex circuit.

11. The electrode apparatus of claim 1, wherein the flex circuit has a plurality of branches which are present only on a single lateral side of the trunk region.

12. The electrode apparatus of claim 1, wherein the flex circuit is configured so that no more than three paths emanate from any intersection on the flex circuit.

13. The electrode apparatus of claim 1, wherein the flex circuit is configured so that one or more intersections on the flex circuit exist from which four paths emanate.

14. The electrode apparatus of claim 1, wherein the flex circuit is configured so that all segments of the flex circuit are straight.

15. The electrode apparatus of claim 1, further comprising an electrical cable that terminates on the flex circuit.

16. The electrode apparatus of claim 15, wherein segments of the flex circuit near the distal end of each branch are thinner than at least some of the segments of the flex circuit that are adjacent to the electrical cable.

* * * * *